US009101283B2

(12) United States Patent
Greiser (10) Patent No.: US 9,101,283 B2
(45) Date of Patent: Aug. 11, 2015

(54) METHOD AND MAGNETIC RESONANCE SYSTEM FOR DETERMINING A CODING FOR A FLOW MEASUREMENT AND FOR IMPLEMENTING A FLOW MEASUREMENT WITH THE CODING

(75) Inventor: Andreas Greiser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1403 days.

(21) Appl. No.: 12/629,452

(22) Filed: Dec. 2, 2009

(65) Prior Publication Data
US 2010/0145184 A1 Jun. 10, 2010

(30) Foreign Application Priority Data
Dec. 2, 2008 (DE) .................. 10 2008 060 049

(51) Int. Cl.
*A61B 5/05* (2006.01)
*A61B 5/055* (2006.01)
*A61B 5/02* (2006.01)
*A61B 5/00* (2006.01)
*G01R 33/563* (2006.01)
*G01R 33/54* (2006.01)

(52) U.S. Cl.
CPC ............. *A61B 5/055* (2013.01); *A61B 5/02007* (2013.01); *A61B 5/7257* (2013.01); *G01R 33/56316* (2013.01); *G01R 33/543* (2013.01); *G01R 33/546* (2013.01)

(58) Field of Classification Search
None
See application file for complete search history.

(56) References Cited

U.S. PATENT DOCUMENTS

| | | | |
|---|---|---|---|
| 5,280,244 A | 1/1994 | Hinks | |
| 6,317,620 B1 | 11/2001 | Ho et al. | |
| 7,145,334 B2 | 12/2006 | Assmann et al. | |
| 7,317,940 B2 | 1/2008 | Assmann | |
| 2003/0225328 A1* | 12/2003 | DeMeester et al. | 600/419 |
| 2005/0203381 A1* | 9/2005 | Harder | 600/420 |
| 2006/0100502 A1* | 5/2006 | Chen et al. | 600/419 |
| 2006/0235669 A1* | 10/2006 | Charbel et al. | 703/11 |
| 2008/0084206 A1* | 4/2008 | Miyoshi | 324/306 |
| 2009/0161934 A1* | 6/2009 | Zhao | 382/131 |

OTHER PUBLICATIONS

MR Glossary, Siemens Medical.

* cited by examiner

*Primary Examiner* — Unsu Jung
*Assistant Examiner* — Shahdeep Mohammed
(74) *Attorney, Agent, or Firm* — Schiff Hardin LLP (57) ABSTRACT

In a method and magnetic resonance system to determine a flow coding for a flow measurement with the magnetic resonance system, in order to determine the optimal flow coding, a flow pre-measurement with multiple different flow codings is conducted within a slice within a body to be examined, each of these codings allowing flow velocities to be detected with a sensitivity dependent on the respective coding. A velocity distribution of the non-slice-location-specific flow velocity values is generated from all of the results of this flow pre-measurement by a common Fourier transformation. The optimal flow coding for the flow measurement is then determined based on this velocity distribution.

26 Claims, 9 Drawing Sheets

METHOD AND MAGNETIC RESONANCE SYSTEM FOR DETERMINING A CODING FOR A FLOW MEASUREMENT AND FOR IMPLEMENTING A FLOW MEASUREMENT WITH THE CODING

BACKGROUND OF THE INVENTION

1. Field of the Invention

The present invention concerns a method to determine as optimal a coding as possible for a flow measurement in a magnetic resonance system. The present invention also concerns a method to conduct a flow measurement with the determined optimal coding. The invention also concerns a magnetic resonance system to implement such methods.

2. Description of the Prior Art

In order to operate with as optimal a speed coding as possible in a phase contrast flow measurement conducted with a magnetic resonance system, according to the prior art time-consuming measurements must be used. If the flow coding is too strong, signal aliasing (folding) occurs in the phase contrast image, in particular in a vessel, this signal aliasing making a quantitative evaluation of the measurement data of the phase contrast flow measurement impossible. Conversely, if the flow coding is too weak, the contrast in the flow representation is too low and the precision in the flow quantification is likewise negatively affected.

According to the prior art, the following methods for determination of as optimal a flow coding as possible for a phase contrast flow measurement are known:

The optimal coding in a post-processing is determined via one or more (fast) prior measurement(s) and evaluation(s) with a coding determined beforehand. However, this is complicated and time-consuming since the flow measurement must thereby be repeated at least once, and additionally the measurement data must be loaded into a post-processing environment during the measurement workflow and be analyzed there.

In a prior measurement, phase contrast measurement data with different codings are measured in a protocol. A user visually decides in which coding only a small amount of aliasing has occurred. This coding is then defined as optimal and used in the phase contrast flow measurement for flow quantification. In addition to the likewise increased measurement effort, this method is imprecise since corresponding compromises in the spatial and temporal resolution are necessary given a use of multiple codings in a flow measurement, such that the determined optimal coding does not necessary exhibit optimal results in the actual flow measurement.

SUMMARY OF THE INVENTION

An object of the present invention is therefore to at least ameliorate the problems according to the prior art in the determination of an optimal flow coding or in the implementation of a flow measurement.

This object is achieved in accordance with the present invention by a method to determine a flow coding (VENC: "Velocity ENCoding value") for a flow measurement with a magnetic resonance system. A flow measurement is conducted with multiple different flow codings in a slice within a body to be examined. Each of these codings, flow speeds are thereby detected with a sensitivity dependent on the respective coding. The sensitivity is thereby in particular defined by the ratio of phase and flow speed, meaning that the sensitivity is higher the greater the phase at a specific flow speed. Therefore, a distribution of flow speeds can be recorded from the entirety of the measurement results detected with different flow speeds. A distribution of flow speeds or flow speed values within the slice or, respectively, within the respective excited volume is thus determined via a Fourier transformation from measurement results of this flow measurement. The coding with which the actual flow measurement can be implemented is then determined from this distribution of flow speed values.

According to the invention, a "flow coding" or a "coding for a flow measurement" means a bipolar gradient pulse pair. A bipolar gradient pulse pair consists of two gradient pulses in different directions but with the same strength. Parameters of these gradient pulses are the magnetic field strength and the duration with which the respective gradient pulse is activated. Since the two gradient pulses have the same strength, the product of the local magnetic field strength and the duration of both gradient pulses is the same (the 0th gradient moment is thus equal). In other words, different gradient pulse pairs are used in the flow measurement described in the preceding for determination of the optimal flow coding, and the corresponding measurement results of this special flow measurement are registered, meaning that the 1st gradient moment is thereby correspondingly varied. A velocity spectrum can then be determined from these measurement data by means of a Fourier transformation.

A "velocity distribution" or a "velocity spectrum" means a type of specification that indicates how often a corresponding velocity (or a velocity value) occurs in the respective excited volume.

For example, the flow measurement to determine the velocity distribution can thereby ensue such that the slice is excited with a first flow coding in a first step and then a first signal of this slice is acquired. The slice is then excited with a second flow coding in a second step and a second signal of this slice is acquired. This is implemented for 16 steps, for example, therefore with 16 different flow codings. These (for example) 16 acquired signals are Fourier-transformed, whereby the velocity distribution results. In the velocity distribution determined in such a manner, none of these velocities can be associated with a specific location within the slice, as is the case in a normal flow measurement according to the prior art. Rather, this is a velocity applicable for the entire slice (or the entire excited volume).

The method according to the invention advantageously requires neither a user interaction nor the implementation of a laborious post-processing. Therefore, the method according to the invention for determination of the optimal coding for a flow measurement can advantageously be implemented together with the actual flow measurement in which the optimal coding determined beforehand is used, since this leads to no significant extension of the measurement duration in comparison to a method in which only the actual flow measurement is conducted.

The optimal coding can be determined such that that coding with which a predetermined percentile (for example 95%) of the flow speed values determined in the flow measurement implemented beforehand is detected is selected as an optimal coding. Naturally, it is also possible to define the coding such that the highest measured velocity can still be detected with the coding, which would essentially correspond to a percentile of 100%. In the selection of this percentile, and therefore in the determination of the optimal coding, a signal-to-noise ratio in the flow measurement conducted beforehand can also be taken into account so that the percentile—and therefore the strength of the coding—is, for example, selected to be lower the higher the signal-to-noise ratio.

Within the scope of the present invention, a method for flow measurement is also provided with a magnetic resonance system that includes the following steps:

Measurement data are acquired by means of an MR angiogram in a volume within a body to be examined. Depending on specifications or inputs, a vessel within the volume is defined by means of the measurement data acquired from the angiogram. Dimensions and an orientation of the previously determined vessel are determined via the measurement data acquired from the angiogram. A slice for the flow measurement is determined depending on these dimensions and on the orientation of the previously determined vessel. According to the method according to the invention that is described in the preceding, the optimal coding the for subsequent flow measurement to be implemented in the slice is defined within the preciously determined slice. The actual flow measurement is implemented in the predetermined slice by means of the optimal coding defined in advance.

In summary, the method according to the invention for flow measurement in particular integrates a quantitative MR phase contrast flow measurement into an MR angiography method or, respectively, an MR angiography workflow. The flow coding necessary for MR phase contrast flow measurement is thereby determined automatically, without user interaction and within the MR angiography method. In contrast to the offline evaluation of the flow measurement that is known from the prior art, a robust online calculation of the flow parameters (i.e. a calculation in the course of the angiogram) is therefore possible so that nothing stands in the way of a use of the method according to the invention in everyday clinical situations.

Via the method according to the invention, the flow measurement (for example a phase contrast flow measurement) can be implemented significantly more easily in comparison to the prior art, and therefore can be implemented more quickly and in a reproducible manner (i.e. two phase contrast flow measurements conducted on the same subject lead to nearly the same results). Moreover, the results of the flow measurement are more precise since the flow measurement is implemented with a flow coding which is automatically adapted to the flow velocities prevailing in the slice.

The angiogram by means of which the measurement data are acquired to determine the vessel can on the one hand be a time-of-flight angiogram or a phase contrast angiogram. The angiogram can thereby be a CE angiogram (contrast enhanced angiogram) or a Non-CE angiogram (an angiogram operating without contrast agent).

The dimensions and the orientation of the vessel are thereby advantageously determined by means of a segmentation algorithm. Vessel properties with which the slice planning (arrangement or formation of the slice) can be additionally improved can also be determined in this segmentation.

To determine the vessel in which the flow measurement is to be implemented, in particular the measurement data acquired via the angiogram are presented on a display in graphical form such that the vessels situated within the volume are thereby graphically represented in a form that is understandable to a person. It is thereby possible that the vessel in which the flow measurement is to be implemented is marked on the display (for example by a physician) in order to thereby define the vessel for the subsequent method steps proceeding automatically.

With the marking with which the vessel to be examined is determined, a specific point of interest within the vessel can thereby also be defined. Therefore it is advantageous when a slice to be planned for the flow measurement runs exactly through this point or comprises this point.

According to an embodiment according to the invention, information about the dimensions of the vessel (which in particular is determined by means of a segmentation algorithm) is used as a boundary condition for the flow pre-measurement in that the volume excited during the flow pre-measurement is adapted precisely to this vessel diameter. Expressed in another way, according to this embodiment the volume which corresponds to an intersection between the slice and the vessel is determined exactly, wherein this volume then is excited to determine the optimal flow coding.

The determination of the optimal coding for the actual flow measurement can thereby also be conducted depending on the heart beat phase. For this the method described in the preceding is implemented for every heart beat phase to determine the optimal coding for the actual flow measurement.

The precision of the flow measurement is thereby specifically optimized for every heart beat phase of the respective patient to be examined. For example, given difficult flow relationships (for example reflux, shunt quantification) this can produce a significant improvement of the measurement results in comparison to flow measurements in which the same flow coding is used in all heart beat phases.

The present invention also encompasses a magnetic resonance system for flow measurement. The magnetic resonance system has a control unit that controls a scanner (data acquisition unit) of the magnetic resonance system, a receiver device that receives signals acquired by the scanner, and a computer that evaluates the acquired signals to implement a flow measurement. The magnetic resonance system is designed to execute a flow measurement with different codings (instead of only one coding) within a slice of a body to be examined. A flow speed is thereby determined with each of these codings. Moreover, computer of the magnetic resonance system generates a distribution of flow velocity values (a velocity spectrum) within the slice by a Fourier transformation depending on the results of the flow measurement implemented with multiple different codings. The computer determines an optimal coding for a flow measurement to be implemented with the coding from the distribution of these flow velocity values.

The present invention also encompasses a magnetic resonance system for flow measurement having a control unit that controls a scanner of the magnetic resonance system, a receiver device that receives signals acquired by the scanner, and a computer that evaluates the acquired signals to implement a flow measurement, the magnetic resonance system being designed to implement an angiography procedure in order to acquire angiography measurement data of a volume within a body to be examined. Moreover, the magnetic resonance system has an input unit to receive a user input. Depending on this user input, by means of the angiography measurement data the magnetic resonance system able to define a vessel. The dimensions and the orientation of this vessel are determined from the angiography measurement data of the computer. Depending on these dimensions and the orientation of the vessel, the magnetic resonance system generates or plans a slice for the flow measurement. The magnetic resonance system is designed such to also execute a flow measurement with multiple different codings (instead of only one coding) within a slice of a body to be examined. With each of these codings, flow velocities are thereby detected with a sensitivity that is dependent on the respective coding. Moreover, the magnetic resonance system is designed such that its computer can generate a distribution of flow velocity values within the slice of a Fourier transformation depending on the results of the flow measurement implemented with multiple different codings, and such that the computer can determine an optimal coding for a primary flow measurement to be implemented with said coding from the distribution of these flow velocity values. The magnetic resonance system implements the primary flow measurement with the previously determined flow coding.

The advantages of the two magnetic resonance system presented in the preceding essentially correspond to the advantages of the corresponding methods according to the invention which have been presented in detail in the preceding.

Moreover, the present invention also encompasses a computer-readable medium that can be loaded into a memory of a programmable controller or a computer of a magnetic resonance system. All or various embodiments of the method according to the invention that are described in the preceding can be executed by programming instructions with which the medium is encoded, when the instructions run on the controller. The medium requires possible program components (for example libraries and auxiliary functions) in order to realize the corresponding embodiments of the method.

The electronically readable data medium (for example a DVD, a magnetic tape or a USB stick) is encoded with electronically readable control information, in particular software. When this control information (software) is read from the data medium and is stored in a controller or computer of a magnetic resonance system, all embodiments according to the invention of the method described in the preceding can be implemented.

The present invention is particularly suitable to implement a phase contrast flow measurement within an angiography workflow by means of a magnetic resonance system. Naturally, the present invention is not limited to this preferred application field but rather can also be used for other types of a flow measurement with a magnetic resonance system, for example.

DESCRIPTION OF THE PREFERRED EMBODIMENTS

Figure 1:
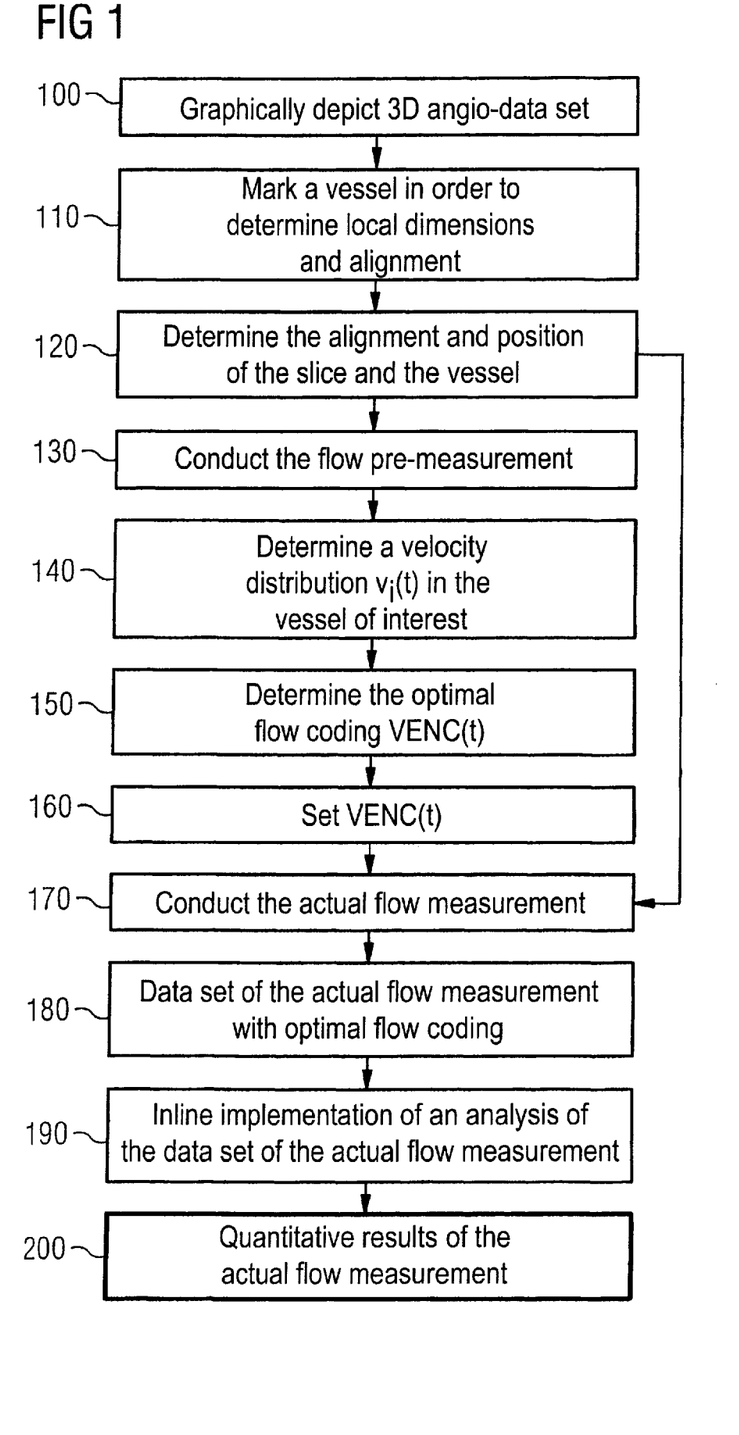
FIG. 1 is a flowchart of a flow measurement with an automatic optimization of the flow coding in accordance with the invention.

FIG. 1 shows a flow plan of a flow measurement with an automatic optimization of the flow coding that is used.

A three-dimensional angiogram is implemented in Step 100 and the data set that is thereby obtained is graphically depicted.

A vessel which is graphically shown by means of the data set obtained via the angiogram is marked in Step 110 in order to determine dimensions of the vessel (for example a diameter and a curvature radius) as well as an alignment of the vessel via this marking.

The position or orientation of a slice is determined in the next Step 120 using the dimensions and the alignment of the vessel such that an optimal measurement of flow speeds within the vessel can ensue by means of this slice.

In the event that the flow coding for the actual flow measurement which is to be implemented in the predetermined slice is already known (for example since it was already defined beforehand), the workflow branches to Step 170. Otherwise, the method according to the invention for determination of a coding is implemented for a flow measurement as it is presented with Steps 130-160.

A flow pre-measurement in which a volume within the vessel is selectively excited is implemented in Step 130. Various flow codings are applied so that the data that are thereby acquired enables (via a Fourier transformation) the generation of an optimally complete velocity spectrum of all flow speeds occurring in the vessel.

Such a velocity spectrum or such a velocity distribution $v_i(t)$ in the vessel of interest is determined with Step 140. This speed distribution $v_i(t)$ is time-dependent since (for example) it depends on the respective heart beat phase of the patient to be examined.

In Step 160 this optimal flow coding VENC(t) that was determined in advance is set in order to then implement the actual flow measurement with this optimal flow coding in the next Step 170. A data set of the actual flow measurement which is implemented with the optimal flow coding is yielded in 180 as a result.

An analysis of this data set is implemented inline in the next Step 190 in order to be able to then show the quantitative results of the actual flow measurement in 200.

Figure 2:
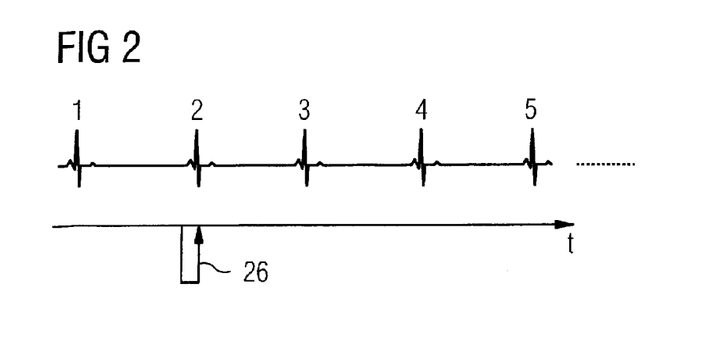
FIG. 2 shows an EKG in order to depict when a flow pre-measurement is implemented and when the actual flow measurement is implemented.

Five heart beats are shown in the form of EKGs in FIG. 2. In a predetermined phase of the second heart beat, the optimal flow coding is determined by means of the method according to the invention that is described above, which optimal flow coding is designated with the reference character 26. As of the third heart beat, the actual flow measurement is then implemented in turn in the respective predetermined heart beat phase with the optimal flow coding determined in such a manner.

In the following the essential steps of a method according to the invention for flow measurement are presented using FIGS. 3 through 9.

Figure 3:
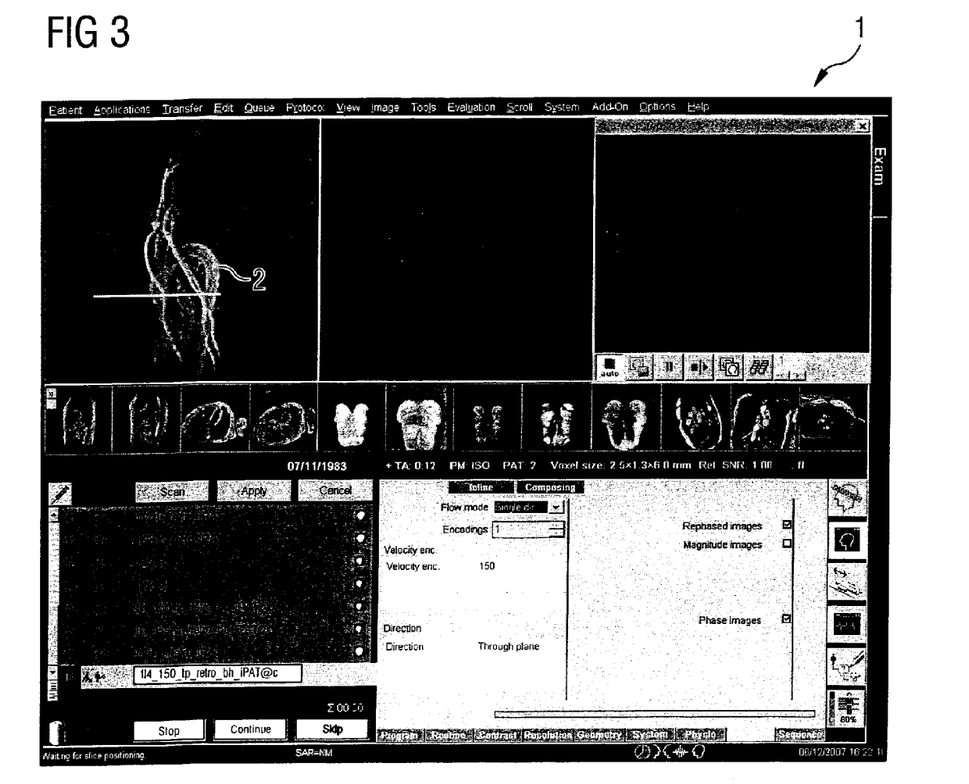
FIG. 3 graphically represents angiography measurement data.

First, angiography measurement data are generated as a reference and graphically presented, as is shown at the top left in a display 1 in FIG. 3.

Figure 4:
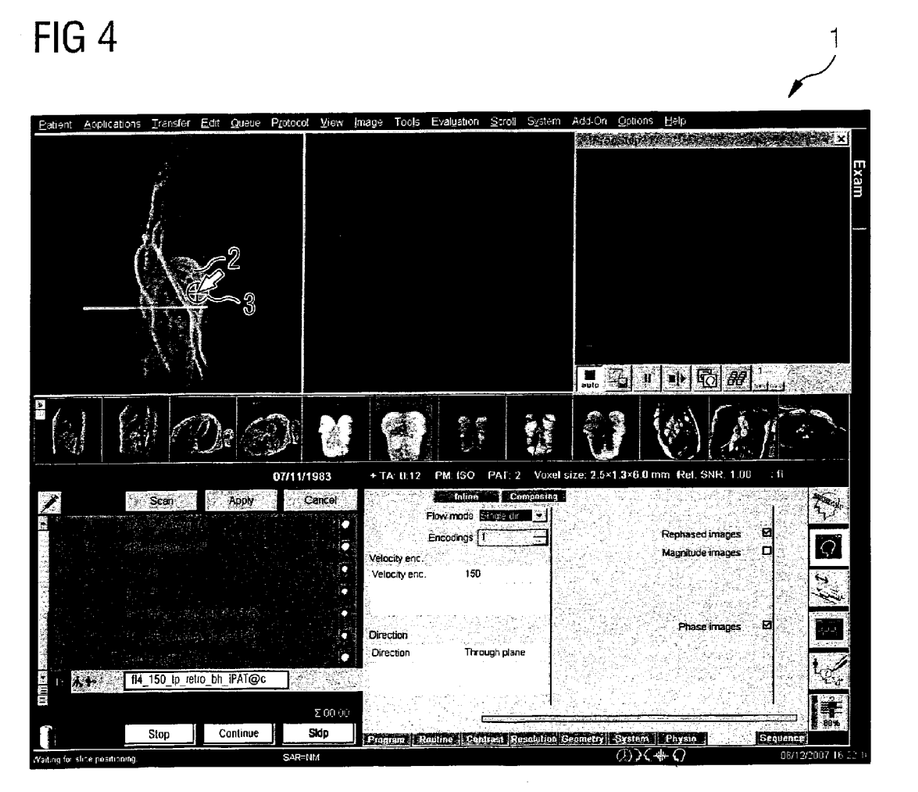
FIG. 4 shows a vessel defined according to the invention using a marking.

For example, in the shown case a physician then marks with a cross-shaped marking 3 that vessel 2 in which a flow measurement should ultimately be conducted. With this marking 3 a spatial point is also defined through which a slice 4 has to run for the flow measurement.

Figure 5:
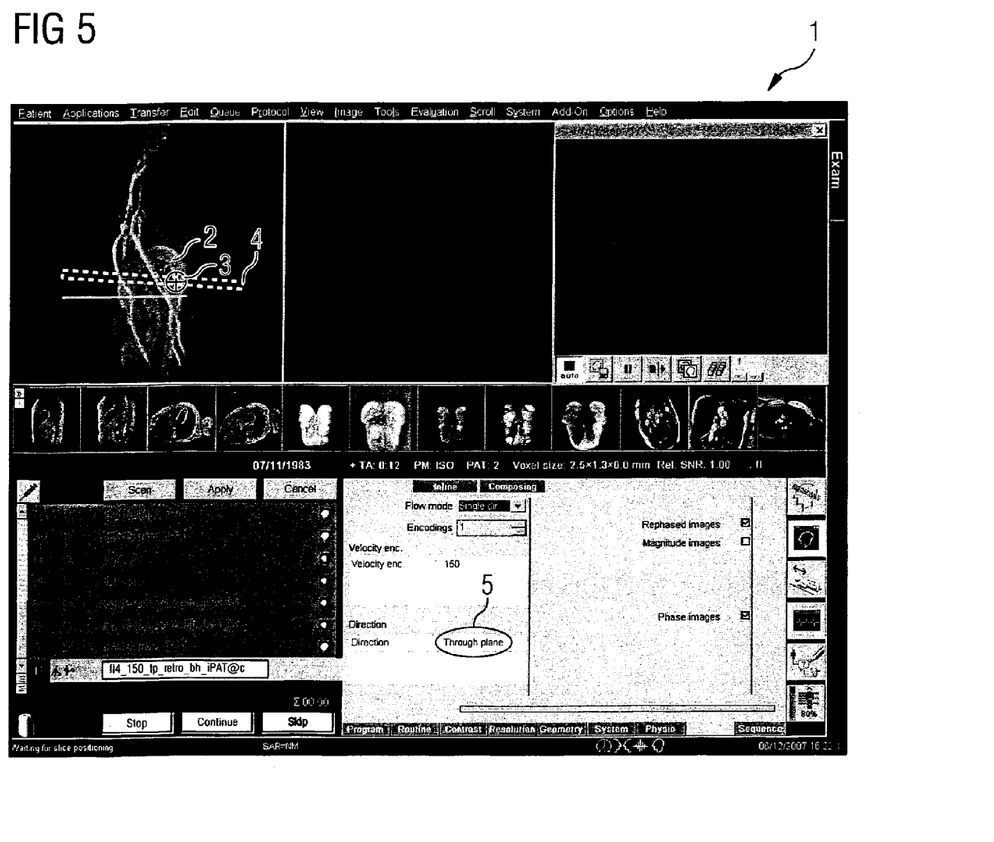
FIG. 5 shows a slice fashioned according to the invention for the implementation of a flow measurement.

Starting from this marking 3, an orientation and a position of a slice 4 are calculated. For this a segmentation algorithm determines the precise bearing or the marked or defined vessel 2 in space. Depending on the position or orientation and position of the vessel 2, the orientation and position of the slice 4 are then determined from this. The slice 4 is usually arranged either perpendicular or parallel to the vessel 2 or to the flow direction within the vessel 2. In the case shown in FIG. 3, the slice 4 is fashioned perpendicular to the vessel 2 and traverses the center point of the marking 3.

How the slice 4 is to be arranged in relation to the marked vessel 2 can be predetermined by the user via the specification of the direction, in this case "Through Plane" 5 (perpendicular to the flow direction).

In order to now be able to conduct a phase contrast flow measurement for the pre-planned slice 4, the flow coding that is necessary for this must be determined in advance. Within the scope of a flow pre-measurement, a flow measurement is conducted in real time in "Q-space" at a first heart beat (corresponds to the heart beat 2 in FIG. 2). In this "Q-space" measurement it is not a single flow coding—and thus a corresponding spatial distribution of the velocities—that is integrated into a normal imaging sequence, as in a conventional phase contrast flow measurement. Rather, via a selective excitation a larger volume (for example comprising the entire vessel segment 2 of interest) is excited. However, instead of a single flow coding a plurality of different flow codings is thereby applied in this volume so that the measured data of this flow pre-measurement allow the generation of an entire velocity spectrum. The distribution of the various velocities within the excited volume can thus be acquired from this spectrum. According to the invention, all relevant information in order to calculate the optimal flow coding for the primary flow measurement or, respectively, actual flow measurement following at the next heart beat are thus provided by the real-time "Q-space" measurement at the first heart beat. Heart phase-dependent, optimal flow coding values can thereby be determined and used in the primary flow measurement.

The "Q-space" can be imagined as a counter-space or Fourier space.

The actual phase contrast flow measurement is conducted for the slice 4 planned beforehand is then conducted with the optimal flow coding determined in such a manner.

Figure 6:
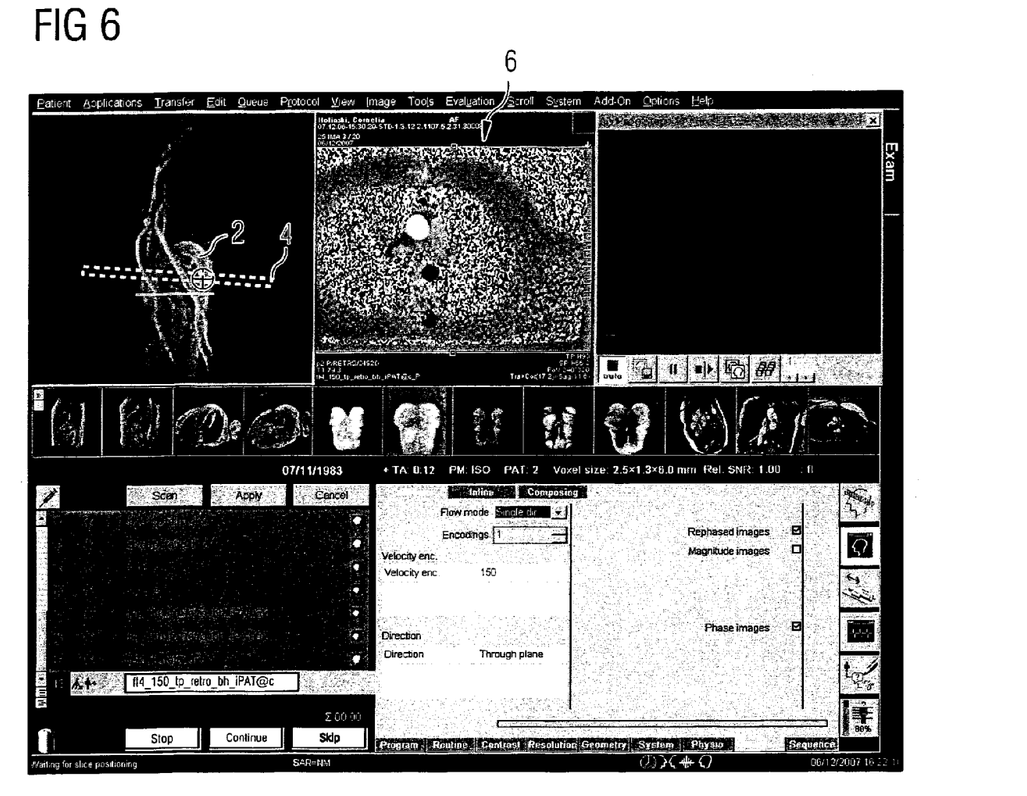
FIG. 6 shows measurement data of a phase contrast flow measurement according to the invention.
Figure 8:
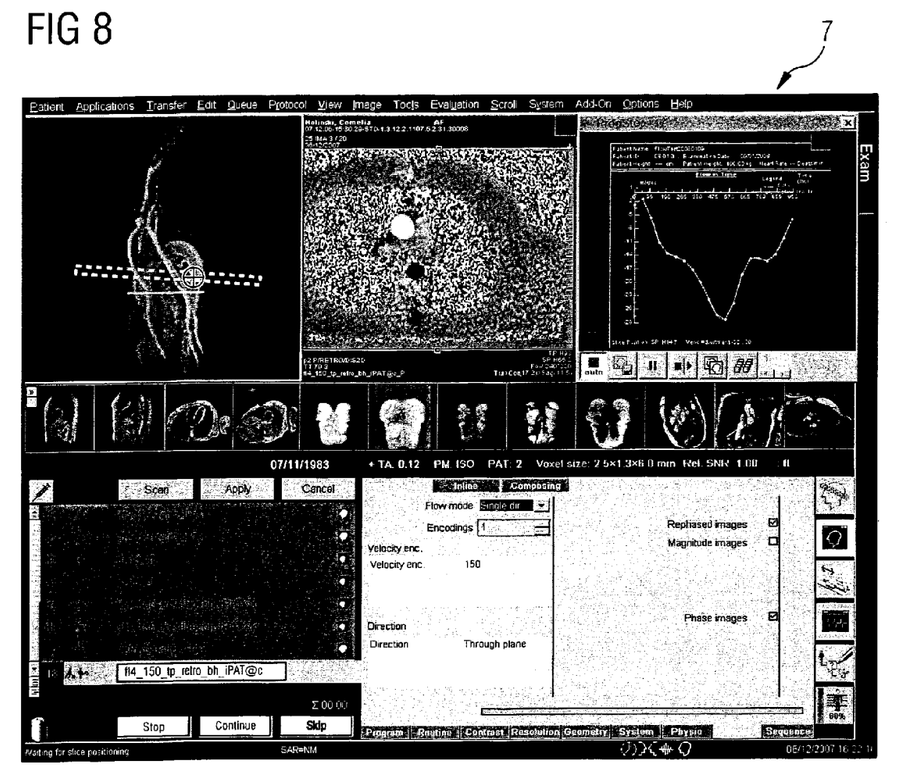
FIG. 8 shows flow speed over time for a specific region.

A graphically presented result of the results acquired via the phase contrast flow measurement is depicted in a display 6 at the right, next to the angio-presentation 1 in FIG. 8.

Figure 7:
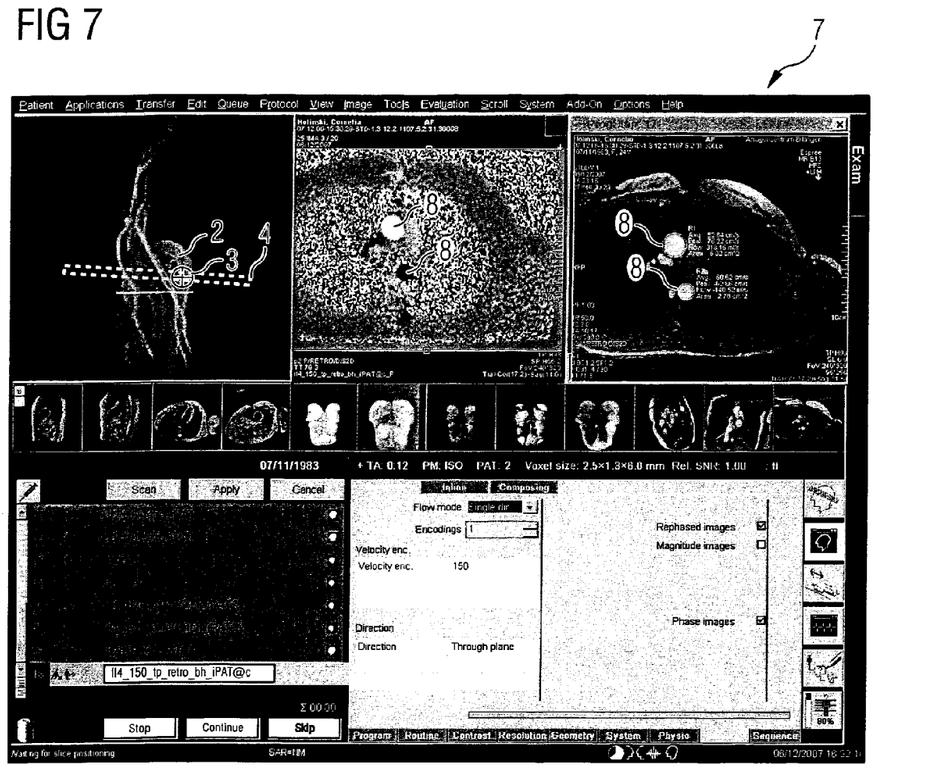
FIG. 7 shows numerical flow parameters for important regions within a slice, superimposed on a graphical representation of this slice.

The measurement data acquired by means of the phase contrast flow measurement are analyzed inline or online (i.e. during the method and not within the framework of a postprocessing) and corresponding flow parameters are generated which are shown at the right on a display 7 (next to the display 6 of the phase contrast flow measurement).

In other words, within the framework of an angiogram both the optimal flow coding can be determined and the results of the flow measurement can be acquired, evaluated and presented while the patient is located within the tomograph of the magnetic resonance system.

In the presentation in FIG. 7, the flow information for important regions within the slice 4 are represented in numerical form. For this regions within the slice 4 in which a significantly similar (high) flow speed is present are determined by means of a segmentation algorithm which can also access results of the angiogram conducted beforehand. In FIG. 7 the two regions marked with the reference characters 8 are thereby regions which are also to be recognizable in the phase contrast image 6.

The respective following measurement results are presented in numerical form, spatially next to these regions 8 shown in the display 7:
- the average flow speed within the corresponding region 8 (in cm/s)
- the peak flow speed within the corresponding region 8 (in cm/s)
- the fluid throughput in the corresponding region 8 (in ml/s)
- an area which is taken up by the respective region 8 (in $cm^2$)

Figure 9:
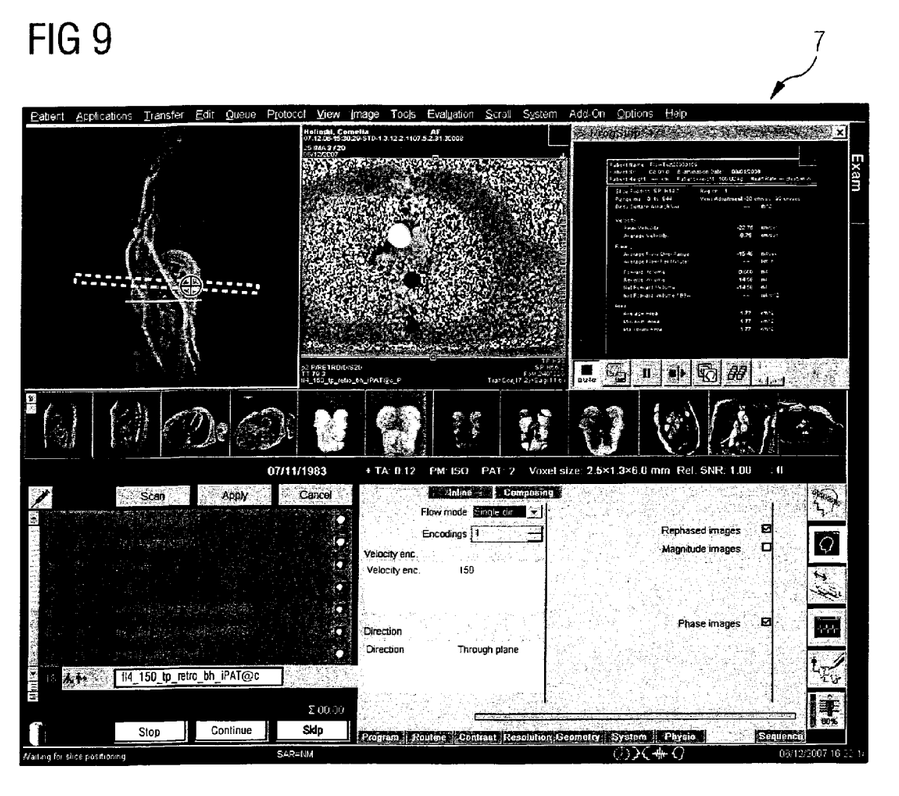
FIG. 9 shows a numerical representation of specific flow information for a specific region within the slice.

Additional possibilities for a presentation of the results of the phase contrast flow measurement are shown in FIG. 8 and FIG. 9. A flow speed over time for a specific region in the slice 4 is thereby shown in the display 7 of FIG. 8 while specific flow information (speed, flow quantity per time, area) is indicated in the display 7 of FIG. 9.

Figure 10:
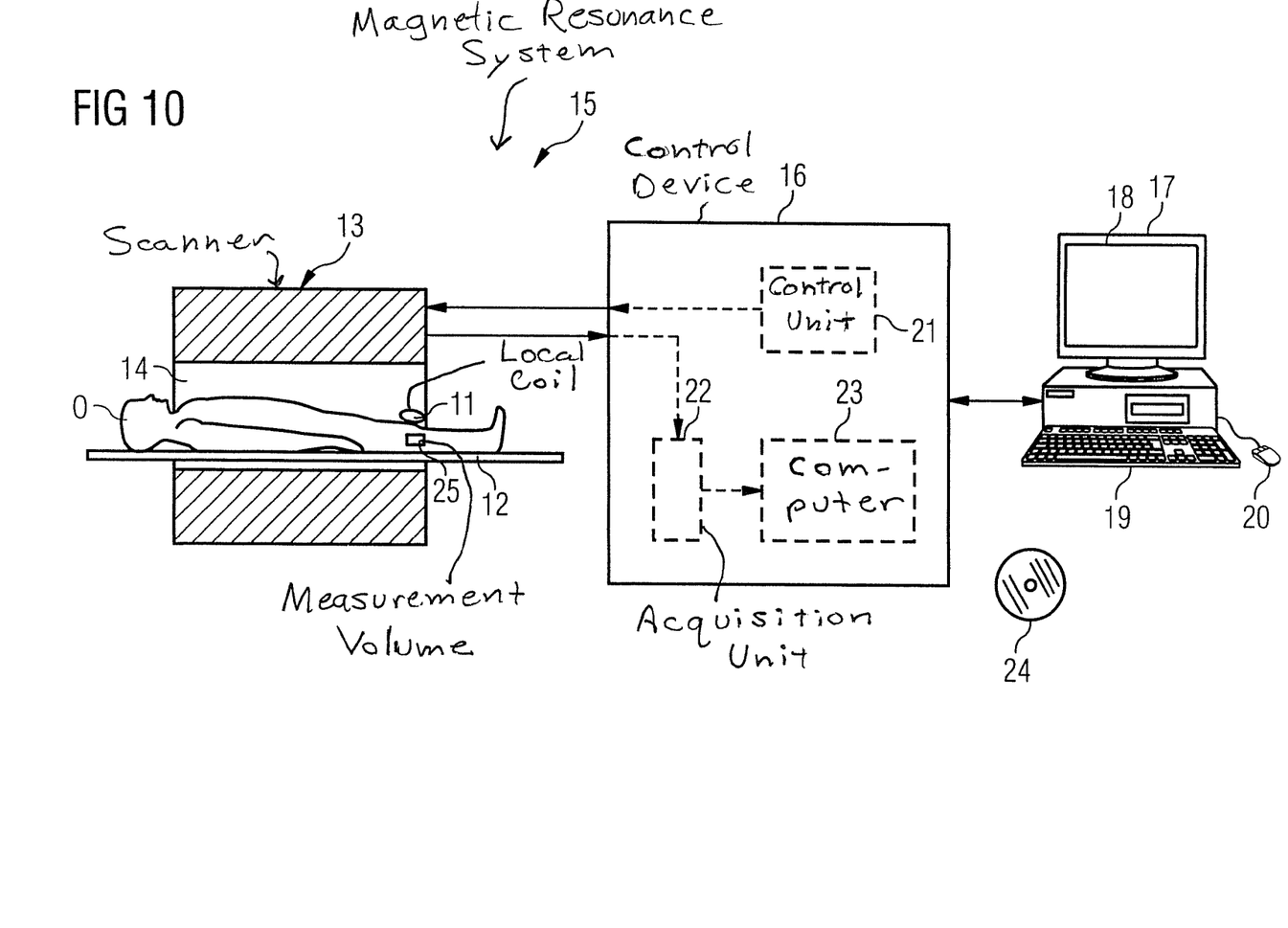
FIG. 10 schematically shows a magnetic resonance system according to the invention.

A magnetic resonance system 15 according to the invention is schematically represented in FIG. 10. The magnetic resonance system 15 essentially has a scanner 13 with which the magnetic field necessary for the MR examination is generated in a measurement space 14, a table 12, a control device 16 with which the scanner 13 is controlled and MR data from the scanner 13 are acquired, and a terminal 17 connected to the control device 16.

The control device 16 has a control unit 21, an acquisition unit 22 and a computer 23. During an MR examination (for example an angiogram or a flow measurement), MR data are acquired by the acquisition unit 22 of the scanner 13, wherein the scanner 13 is controlled by the control unit 21 such that angiography measurement data are acquired in an angiogram by a local coil 11 from a measurement volume 25 which is located inside the body of a patient O lying on the table 12.

The computer 13 then prepares the angiography measurement data and measurement data of the flow measurement such that they can be graphically presented on a monitor 18 of the terminal 17. In addition to the graphical presentation of the angiography measurement data and measurement data of the flow measurement, a vessel 2 can be provided with a marking 4 and further specifications for the implementation of the angiogram and the flow measurement can be made by a user with the terminal 17 which, in addition to the monitor 18, comprises a keyboard 19 and a mouse 20. The control device 16 is also in the position (by means of the computer 23) to implement the method according to the invention to determine the optimal coding for flow measurement.

The software for the control device 16 can also be loaded via the terminal 17 into said control device 16, in particular into the computer 23. This software of the control device 16 thereby also comprises the method according to the invention for determination of a coding for a flow measurement and the method according to the invention for implementation of a flow measurement. This software can likewise be stored on a DVD 24 so that this software can then be read from the DVD 24 by the terminal 17 and be copied to the control device 16.

Although modifications and changes may be suggested by those skilled in the art, it is the intention of the inventor to embody within the patent warranted hereon all changes and modifications as reasonably and properly come within the scope of his or contribution to the art.

I claim as my invention:

1. A method for determining a coding for a magnetic resonance flow measurement in a magnetic resonance system, comprising:

operating a magnetic resonance scanner to implement a flow pre-measurement by emitting at least one radio-frequency pulse that excites nuclear spins in a flowing medium within an excited volume within an examination subject in whom a subsequent diagnostic flow measurement is to be conducted, and by activating magnetic gradient pulses in a plurality of different pulse configurations that respectively produce multiple, different codings that cause flow velocities of said flowing medium to be detected with a respective, different detection sensitivity that is dependent on the respective coding, and each of said codings individually causing a respective magnetic resonance signal to be emitted from said excited volume that is dependent on the respective sensitivity caused by the respective coding;

operating said magnetic resonance scanner to detect said magnetic resonance signals and, from a processor provided with the detected magnetic resonance signals, entering said magnetic resonance signals into an electronic memory organized as Q-space, said Q-space being a Fourier transform of a distribution of various velocities that occur within the excited volume;

in said processor, implementing a Fourier transformation on said Q-space, to produce a compilation of flow velocity values that occur in within the excited volume, said compilation being independent of spatial locations at which said velocity values occur within the excited volume, and showing how often respective flow velocity values occur within the excited volume;

in said processor, automatically determining a determined coding for said diagnostic flow measurement from said compilation of said flow velocity values as a coding, from among said multiple, different codings, that causes a predetermined percentile of the distribution of said flow velocity values to be detected; and making said determined coding available at an output of said processor, in an electronic form configured to operate said magnetic resonance scanner to implement said diagnostic flow measurement with said determined coding.

2. A method as claimed in claim 1 comprising implementing said flow-pre-measurement for different heart beat phases to determine said determined coding for said flow measurement for each of said heart beat phases.

3. A method as claimed in claim 1 wherein said gradient pulses are bipolar gradient pulses, each having a first moment, and comprising determining said determined coding as being a coding produced by a bipolar gradient pulse, among said plurality of bipolar gradient pulses, that has a first moment that causes said predetermined percentile of said flow velocity values to be detected.

4. A method for magnetic resonance flow measurement in a magnetic resonance system, comprising:

operating a magnetic resonance scanner to obtain magnetic resonance angiography data from a volume within an examination subject in whom a subsequent diagnostic flow measurement is to be conducted;

supplying said angiography measurement data to a processor and providing a user input to said processor and, in said processor, determining a vessel in said volume from said angiography measurement data, dependent on said user input;

in said processor, automatically determining dimensions and an orientation of said vessel from said angiography measurement data;

in said processor, automatically determining a slice in the examination subject for implementing a diagnostic flow measurement therein dependent on said dimensions and said orientation of said vessel;

before conducting said diagnostic flow measurement, operating said magnetic resonance scanner to implement a flow pre-measurement by emitting at least one radio-frequency pulse that excites nuclear spins in a flowing medium within said slice in said examination subject, and by activating magnetic gradient pulses in a plurality of different pulse configurations that respectively produce multiple, different codings that cause flow velocities of said flowing medium to be detected with a respective, different detection sensitivity that is dependent on the respective coding, and each of said codings individually causing a respective magnetic resonance signal to be emitted from said excited slice that is dependent on the respective sensitivity caused by the respective coding;

operating said magnetic resonance scanner to detect said magnetic resonance signals and providing the detected magnetic resonance signals to said processor and, from said processor, entering said magnetic resonance signals into an electronic memory organized as Q-space, said Q-space being a Fourier transform of a distribution of various velocities that occur within the excited slice;

in said processor, implementing a Fourier transformation on said Q-space, to produce a compilation of flow velocity values that occur in within the excited slice, said compilation being independent of spatial locations at which said velocity values occur within the excited slice, and showing how often respective flow velocity values occur within the excited slice;

in said processor, automatically determining a determined coding for said diagnostic flow measurement from said compilation of said flow velocity values as a coding, from among said multiple, different codings, that causes a predetermined percentile of the distribution of said flow velocity values to be detected; and operating said magnetic resonance scanner to implement said diagnostic flow measurement in said slice using said determined coding, and thereby producing a diagnostic flow measurement data file, and making said diagnostic flow measurement data file available in electronic form at an output of said processor.

5. A method as claimed in claim 4 comprising determining said dimensions and orientation of said vessel by image segmentation.

6. A method as claimed in claim 5 comprising defining said vessel by graphically presenting said angiography measurement data at a display wherein said vessel within said volume is graphically depicted, and providing said vessel with a marking.

7. A method as claimed in claim 6 comprising employing a point as said marking and defining said slice as a slice that contains said point.

8. A method as claimed in claim 4 comprising exciting nuclear spins only in a volume within said vessel in said flow pre-measurement.

9. A method as claimed in claim 4 comprising implementing said flow-pre-measurement for different heart beat phases to determine said determined coding for said flow measurement for each of said heart beat phases.

10. A method as claimed in claim 4 comprising implementing said flow measurement as a phase contrast flow measurement.

11. A method as claimed in claim 4 wherein said gradient pulses are bipolar gradient pulses, each having a first moment, and comprising determining said determined coding as being a coding produced by a bipolar gradient pulse, among said plurality of bipolar gradient pulses, that has a first moment that causes said predetermined percentile of said flow velocity values to be detected.

12. A magnetic resonance apparatus, comprising:
a magnetic resonance scanner;
an electronic memory;
a computer configured to operate said magnetic resonance scanner to implement a flow pre-measurement by emitting at least one radio-frequency pulse that excites nuclear spins in a flowing medium within an excited volume within an examination subject in whom a subsequent diagnostic flow measurement is to be conducted, and by activating magnetic gradient pulses in a plurality of different pulse configurations that respectively produce multiple, different codings that cause flow velocities of said flowing medium to be detected with a respective, different detection sensitivity that is dependent on the respective coding, and each of said codings individually causing a respective magnetic resonance signal to be emitted from said excited volume that is dependent on the respective sensitivity caused by the respective coding;

said computer being configured to operate said magnetic resonance scanner to detect said magnetic resonance signals and to enter said magnetic resonance signals in Q-space in said electronic memory, said Q-space being a Fourier transform of a distribution of various velocities that occur within the excited volume;

said computer being configured to implement a Fourier transformation on said Q-space, to produce a compilation of flow velocity values that occur in within the excited volume, said compilation being independent of spatial locations at which said velocity values occur within the excited volume, and showing how often respective flow velocity values occur within the excited volume;

said computer being configured to automatically determine a determined coding for said diagnostic flow measurement from said compilation of said flow velocity values as a coding, from among said multiple, different codings, that causes a predetermined percentile of the distribution of said flow velocity values to be detected; and said computer being configured to make said determined coding available at an output of said computer, in an electronic form configured to operate said magnetic resonance system to implement said diagnostic flow measurement with said determined coding.

13. A magnetic resonance system as claimed in claim 12 wherein said computer is configured to implement said flow-pre-measurement for different heart beat phases to determine said determined coding for said flow measurement for each of said heart beat phases.

14. A magnetic resonance system as claimed in claim 12 wherein said computer is configured to operate said magnetic resonance data acquisition unit to implement said flow pre-measurement by activating, as said gradient pulses, bipolar gradient pulses each having a first moment, and wherein said computer is configured to determine said determined coding as a coding produced by a bipolar gradient pulse, among said plurality of bipolar gradient pulses, that has a first moment that causes said predetermined percentile of said flow velocity values to be detected.

15. A magnetic resonance apparatus comprising:
a magnetic resonance scanner;
an electronic memory;
a computer configured to operate said magnetic resonance scanner to obtain magnetic resonance angiography data from a volume within an examination subject in whom a subsequent diagnostic flow measurement is to be conducted;
said computer being supplied with said angiography measurement data and being configured to receive a user input and to determine a vessel in said volume from said angiography measurement data, dependent on said user input;

said computer being configured to automatically determine dimensions and an orientation of said vessel from said angiography measurement data;
said computer being configured to automatically determine a slice in the examination subject for implementing a diagnostic flow measurement therein dependent on said dimensions and said orientation of said vessel;
said computer being configured to operate said magnetic resonance scanner, before said diagnostic flow measurement is conducted, to implement a flow pre-measurement by emitting at least one radio-frequency pulse that excites nuclear spins in a flowing medium within said slice within the examination subject, and by activating magnetic gradient pulses in a plurality of different pulse configurations that respectively produce multiple, different codings that cause flow velocities of said flowing medium to be detected with a respective, different detection sensitivity that is dependent on the respective coding, and each of said codings individually causing a respective magnetic resonance signal to be emitted from said excited slice that is dependent on the respective sensitivity caused by the respective coding;
said computer being configured to operate said magnetic resonance scanner to detect said magnetic resonance signals and to enter said magnetic resonance signals in Q-space in said electronic memory, said Q-space being a Fourier transform of a distribution of various velocities that occur within the excited slice;
said computer being configured to implement a Fourier transformation on said Q-space, to produce a compilation of flow velocity values that occur in within the excited slice, said compilation being independent of spatial locations at which said velocity values occur within the excited slice, and showing how often respective flow velocity values occur within the excited slice;
said computer being configured to automatically determine a determined coding for said diagnostic flow measurement from said compilation of said flow velocity values as a coding, from among said multiple, different codings, that causes a predetermined percentile of the distribution of said flow velocity values to be detected; and
said computer being configured to operate said magnetic resonance scanner to implement said diagnostic flow measurement in said slice using said determined coding, and thereby producing a diagnostic flow measurement data file, and making said diagnostic flow measurement data file available in electronic form at an output of said computer.

16. A magnetic resonance system as claimed in claim 15 wherein said computer is configured to determine said dimensions and orientation of said vessel by image segmentation.

17. A magnetic resonance system as claimed in claim 16 wherein said computer is configured to define said vessel by graphically presenting said angiography measurement data at a display wherein said vessel within said volume is graphically depicted, and providing said vessel with a marking.

18. A magnetic resonance system as claimed in claim 17 wherein said computer is configured to employ a point as said marking and defining said slice as a slice that contains said point.

19. A magnetic resonance system as claimed in claim 15 wherein said computer is configured to operate said magnetic resonance data acquisition unit to excite nuclear spins only in a volume within said vessel in said flow pre-measurement.

20. A magnetic resonance system as claimed in claim 15 wherein said computer is configured to operate said magnetic resonance data acquisition unit to implement said flow-pre-measurement for different heart beat phases to determine said determined coding for said flow measurement for each of said heart beat phases.

21. A magnetic resonance system as claimed in claim 15 wherein said computer is configured to operate said magnetic resonance data acquisition to implement said flow measurement as a phase contrast flow measurement.

22. A magnetic resonance system as claimed in claim 15 wherein said computer is configured to operate said magnetic resonance data acquisition unit to implement said flow pre-measurement by activating, as said gradient pulses, bipolar gradient pulses each having a first moment, and wherein said computer is configured to determine said determined coding as a coding produced by a bipolar gradient pulse, among said plurality of bipolar gradient pulses, that has a first moment that causes said predetermined percentile of said flow velocity values to be detected.

23. A non-transitory, computer-readable data storage medium encoded with programming instructions, said data storage medium being loadable into a computer of a magnetic resonance apparatus, said magnetic resonance apparatus comprising a magnetic resonance scanner and an electronic memory, and said programming instructions causing said computer to:
operate the magnetic resonance scanner to implement a flow pre-measurement by emitting at least one radio-frequency pulse that excites nuclear spins in a flowing medium within an excited volume within an examination subject in whom a subsequent diagnostic flow measurement is to be conducted, and by activating magnetic gradient pulses in a plurality of different pulse configurations that respectively produce multiple, different codings that cause flow velocities of said flowing medium to be detected with a respective, different detection sensitivity that is dependent on the respective coding, and each of said codings individually causing a respective magnetic resonance signal to be emitted from said excited volume that is dependent on the respective sensitivity caused by the respective coding;
operate the magnetic resonance scanner to detect said magnetic resonance signals and enter said magnetic resonance signals in Q-space in said electronic memory, said Q-space being a Fourier transform of a distribution of various velocities that occur within the excited volume;
implement a Fourier transformation on said Q-space, to produce a compilation of flow velocity values that occur in within the excited volume, said compilation being independent of spatial locations at which said velocity values occur within the excited volume, and showing how often respective flow velocity values occur within the excited volume;
automatically determine a determined coding for said diagnostic flow measurement from said compilation of said flow velocity values as a coding, from among said multiple, different codings, that causes a predetermined percentile of the distribution of said flow velocity values to be detected; and
make said determined coding available at an output of said computer, in an electronic form configured to operate said magnetic resonance scanner to implement said diagnostic flow measurement with said determined coding.

24. A data storage medium as claimed in claim 23 wherein said programming instructions cause said computer to operate said magnetic resonance system to implement said flow pre-measurement by activating said gradient pulses as bipolar gradient pulses, each having a first moment, and to determine said determined coding as a coding produced by a bipolar gradient pulse, among said plurality of bipolar gradient pulses, that has a first moment that causes said predetermined percentile of said flow velocity values to be detected.

25. A non-transitory, computer-readable data storage medium encoded with programming instructions, said data storage medium being loadable into a computer of a magnetic resonance apparatus, said magnetic resonance apparatus comprising a magnetic resonance scanner and an electronic memory, and said programming instructions causing said computer to:
operate the magnetic resonance scanner to obtain magnetic resonance angiography data from a volume within an examination subject in whom a subsequent diagnostic flow measurement is to be conducted;
receive a user input and determine a vessel in said volume from said angiography measurement data, dependent on said user input;
automatically determine dimensions and an orientation of said vessel from said angiography measurement data;
automatically determine a slice in the examination subject for implementing a diagnostic flow measurement therein dependent on said dimensions and said orientation of said vessel;
before conducting said diagnostic flow measurement, operate said magnetic resonance scanner to implement a flow pre-measurement by emitting at least one radio-frequency pulse that excites nuclear spins in a flowing medium within said slice in the examination subject, and by activating magnetic gradient pulses in a plurality of different pulse configurations that respectively produce multiple, different codings that cause flow velocities of said flowing medium to be detected with a respective, different detection sensitivity that is dependent on the respective coding, and each of said codings individually causing a respective magnetic resonance signal to be emitted from said excited slice that is dependent on the respective sensitivity caused by the respective coding;
operate the magnetic resonance scanner to detect said magnetic resonance signals and enter said magnetic resonance signals in Q-space in said electronic memory, said Q-space being a Fourier transform of a distribution of various velocities that occur within the excited volume;
implement a Fourier transformation on said Q-space, to produce a compilation of flow velocity values that occur in within the excited slice, said compilation being independent of spatial locations at which said velocity values occur within the excited slice, and showing how often respective flow velocity values occur within the excited slice;
automatically determine a determined coding for said diagnostic flow measurement from said compilation of said flow velocity values as a coding, from among said multiple, different codings, that causes a predetermined percentile of the distribution of said flow velocity values to be detected; and
operate said magnetic resonance scanner to implement said diagnostic flow measurement in said slice using said determined coding, and thereby producing a diagnostic flow measurement data file, and make said diagnostic flow measurement data file available in electronic form at an output of said computer.

26. A data storage medium as claimed in claim 25 wherein said programming instructions cause said computer to operate said magnetic resonance system to implement said flow pre-measurement by activating said gradient pulses as bipolar gradient pulses, each having a first moment, and to determine said determined coding as a coding produced by a bipolar gradient pulse, among said plurality of bipolar gradient pulses, that has a first moment that causes said predetermined percentile of said flow velocity values to be detected.

* * * * *